United States Patent [19]

Robertson

[11] Patent Number: 5,316,474

[45] Date of Patent: May 31, 1994

[54] DENTAL IMPRESSION TRAY

[76] Inventor: Walter H. Robertson, 16947 Shinedale St., Santa Clarita, Calif. 91351

[21] Appl. No.: 71,969

[22] Filed: Jun. 7, 1993

[51] Int. Cl.[5] ............................................. A61C 9/00
[52] U.S. Cl. ......................................... 433/38; 433/37
[58] Field of Search ........................ 433/37, 38, 42, 43, 433/214, 71

[56] References Cited

U.S. PATENT DOCUMENTS

| | | | |
|---|---|---|---|
| 2,895,219 | 7/1959 | Jones | 433/38 |
| 3,574,259 | 4/1971 | Jones | 433/38 |
| 3,903,602 | 9/1975 | Jones | 433/38 |
| 4,003,132 | 1/1977 | Beck | 433/42 |
| 4,146,963 | 4/1979 | Schreinemakers | 433/37 |
| 4,472,140 | 9/1984 | Lustig | 433/38 |
| 4,689,010 | 8/1987 | Wolfe | 433/38 |

FOREIGN PATENT DOCUMENTS 538242  3/1957  Canada ........................ 433/38

Primary Examiner—Gene Mancene
Assistant Examiner—Nicholas D. Lucchesi
Attorney, Agent, or Firm—Roger A. Marrs

[57] ABSTRACT

A dental impression tray is disclosed herein having a pair of spaced-apart arcuate walls having a common radial center and wherein the opposing wall surfaces define a work area for holding a quantity of dental impression material. A thin plastic embedded fibrous membrane or sheet extends across the work area having its opposite edges attached to the walls and separating the walls into upper and lower wall sections. One end of the walls may or may not support a wire element while the opposite walls' ends are open. The opposing wall surfaces carry a plurality of alternate vertical grooves and rod-like projections disposed in parallel and split horizontally by the fibrous membrane. The root of each projection includes a recessed portion in order to engage with the impression material and a handle attached to an outer wall of the pair outwardly extends anteriorly therefrom. A tongue suppressor structure may be integrated on an inner wall of the pair.

19 Claims, 1 Drawing Sheet

DENTAL IMPRESSION TRAY

BACKGROUND OF THE INVENTION

1. Field of the Invention

The present invention relates to the field of dental instruments, and more particularly to a novel dental impression tray for obtaining an impression of a patient's dentition, including an impression of both the upper and lower arches and registering their relationship to each other in a single procedure.

2. Brief Description of the Prior Art

Prior or conventional impression trays are incapable of taking accurate impressions in a consistent manner. In general, dental trays for obtaining an impression of a patient's dentition include a tray portion contoured to fit within the patient's mouth so that when the patient closes or bites his teeth, an impression is made in the impression material. Initially, the tray is loaded with a suitable setting impression material on both hemispheres of the tray and situated opposite to the desired dentition part whereupon the patient bites into the impression material to form an impression of the dentition in the material. After the impression material sets, it is used as a mold into which plaster or the like can be poured which, upon setting, forms a model of the dentition.

Prior attempts have been made to solve a variety of problems in the use of dental impression trays and one such attempt is disclosed in U.S. Pat. No. 4,689,010. However, problems and difficulties have been encountered which stem largely from the fact that it is difficult to retain the impression material in place during and particularly after the impression bite has been made. At times, the supporting layer for the impression material may be perforated by the sharp teeth of the patient during the taking of the impression. Also, conventional trays do not properly flex during the impression procedure. At the end of the procedure, the tray sometimes reverts to a previous configuration causing distortion of the impression.

Most conventional triple bite trays have experienced problems in the area of distortion. The process of taking the impression allows the impression material which is set within the tray on both sides of the gauze support at which time the patient bites into the unset impression material such as polyvinyliloxane and when the material is set or hardened, the impression tray along with the impression material will be removed from the mouth. It is at this point that the distortion occurs due to the memory found in the plastics or metals used in the construction of the tray. This memory found in the arches connecting the parallel walls is stronger than the memory found in the impression material. As the patient bites down into the impression, the tray flexes in a Buccal/Lingual direction, due to the strength of the muscle of mouth and the design of the walls. Upon removal of the impression and the tray, the memory that is present within the plastics and metals will flex back to the original position it was in prior to the impression being taken. The result is a distorted impression due to the fact that the memory of the impression material especially over the occlusal surfaces, which have exposed the gauze supports, is weaker than the memory of a plastic or metal retro molar arch. Wire allows flexing of the tray so that the memory of the impression material is stronger than that of the wire.

SUMMARY OF THE INVENTION

Accordingly, the above problems and difficulties are overcome by the present invention which provides a novel dental impression tray having a pair of arcuate walls arranged in fixed spaced-apart relationship so as to define a working area between its opposing surfaces. A support material, such as a plastic embedded fibrous layered sheet, extends between the opposing walls and separates the working area into an upper and lower section so as to support the impression material in both hemispheres of the tray in order that both upper and lower impressions can be taken during the same procedure. In one form of the invention, a wire connects the ends of the walls posteriorly. In another form of the invention, the tray may take the form of a quadrant impression while in another form, a full mouth impression can be taken. Also, a tongue suppressor may be included for the convenience of the user and which will assist in the procedure.

Therefore, it is among the primary objects of the present invention to provide a novel dental impression tray which will prevent and avoid distortion of the impression made in an impression material which may be due to the memory found in conventional plastics or metals.

Another object of the present invention is to provide a novel improved dental impression tray which includes anti-distortion means for maintaining the impression material in place so that it will not move or distort while the impression is being made or after the impression has been made when the tray has been removed from the patient's mouth.

A further object of the present invention is to provide a novel dental tray which will permit the taking of accurate impressions for both the upper and the lower arches simultaneously and which will register their relationship to each other in a single step which will allow the tray to flex or adapt to existing dentition.

Yet another object of the present invention is to provide a novel dental tray which includes a tongue retractor integrally incorporated into the tray for the convenience of the user during the impression taking procedure.

Another object resides in the placement of a handle integrally formed on the dental tray which extends anteriorly in a straight manner and which is substantially normal to the wall of the tray on which it is integrally formed.

Still another object of the invention is to provide a dental tray having an outer wall of greater height than its associated inner wall in order that the over-all dimension of the tray is reduced for the convenience and comfort of the patient and the minimizing of unnecessary force on the tray.

Another object resides in providing an impression material retaining means which is exterior of the plurality of retaining ribs and does not require weakening of rib roots at their juncture with the wall on which they are carried.

An important object further resides in constructing the dental tray to permit flexing of the tray so that the memory of the impression material is stronger than that of the arch construction.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DESCRIPTION OF THE PREFERRED EMBODIMENT

Figure 1:
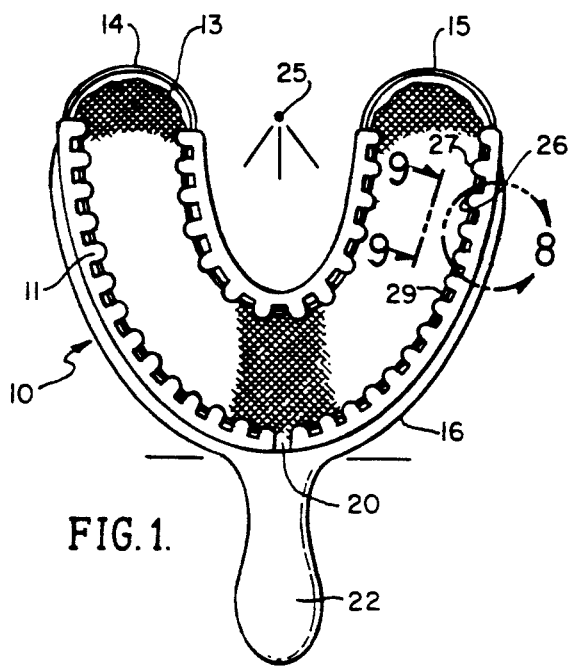
FIG. 1 is a top plan view of the novel dental impression tray incorporating the present invention.

Referring to FIG. 1, the novel dental impression tray of the present invention is illustrated in the general direction of arrow 10 which is adapted for use in obtaining an impression of the posterior or bicuspid and molar part of both the upper and lower dentitions. It is understood that other configurations for obtaining impressions for other areas of the dentition are within the scope of the present invention. The tray 10 includes a pair of arcuate walls referred to in FIG. 1 as an outer wall 11 and an inner wall 12. The inner and outer walls are arranged in fixed spaced-apart relationship so as to define a working area therebetween which is intended to be occupied by a settable impression material. The material does not form a part of the present invention. However, the material is supported on a thin plastic embedded fibrous sheet or membrane, indicated by numeral 13, which has its edge marginal regions attached to the opposing walls 11 and 12 midway between the top and bottom of the walls. The membrane 13 may take the form of a paper, close mesh netting gauze or other plastic or paper-like materials or both. However, it is to be understood that the material is of high strength-to-weight ratio so as to eliminate perforations of the membrane while a dental impression is being made. Also, it must be borne in mind that the membrane 13 supports impression material on opposite sides so that the impression of both upper and lower teeth arches can be taken. Also, it is to be understood that the posterior end of the walls 11 and 12 may be joined by wires 14 and 15 which allow movement of the walls during the taking of the impression and afterwards as the impression material is being cured or set, it will maintain the shape of the wire due to the stronger memory of the impression material over the wire which is weaker in memory. The material of the wires 14 and 15 is of a non-memoric material so that even if the wires are flexed during the impression-taking procedure, the walls will not return to their pre-impression orientation due to the lack of spring-back or any memoric distortion encountered by the wires.

Figure 2:
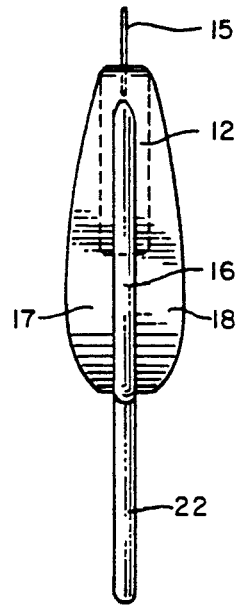
FIG. 2 is a side elevational view of the dental tray shown in FIG. 1.
Figure 3:
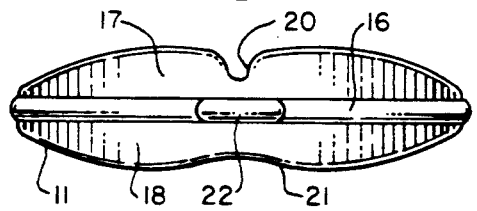
FIG. 3 is an end elevational view of the dental tray shown in FIG. 1.

FIGS. 2 and 3 clearly illustrate that the walls are sectioned by the membrane 13 and an outer frame rib 16 so that numeral 17 represents an upper wall while numeral 18 represents a lower wall. FIG. 2 also illustrates that the outer wall 11 in the upper section 17 includes a depression, identified by numeral 20, which is to accommodate the patient's upper frenum during the impression-taking procedure. A shallower indentation 21 is formed in the lower wall section 18 of wall 11 which is to accommodate the lower frenum of the patient during the impression procedure. Furthermore, an integral handle 22 is formed with the wall 11 and rib 16 that extends anteriorly normal to the wall at the point of attachment.

Figures 8, 9:
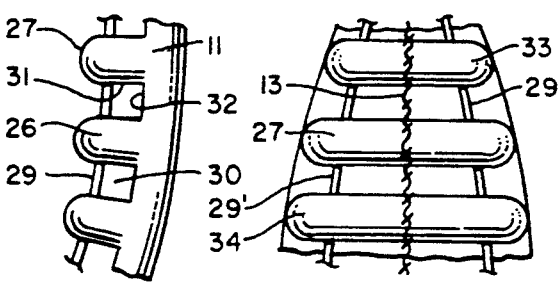
FIG. 8 is a fragmentary plan view of FIG. 1 greatly enlarged to illustrate the impression material retaining means associated with the opposing walls incorporated into the trays illustrated in FIGS. 1, 4 and 6.
FIG. 9 is an enlarged elevational view of a wall used in the versions of the present invention and, in particular, as taken in the direction of arrows 9—9 of FIG. 1.

It is also to be noted in FIG. 1 that the arcuate walls 11 and 12 are arranged so that their inner surfaces are relatively in parallel alignment with respect to one another and that they would share a common radial center, such as indicated by numeral 25. Also, and of prime importance, it can be seen that the inner opposing surfaces of the walls 11 and 12 are provided with a plurality of ribs, such as ribs 26 and 27 that are arranged in spaced-apart parallel relationship and which are normal or perpendicular to the supporting membrane 13. A larger view of these ribs is illustrated in FIG. 8 so that it can be seen that the grooves separating the adjacent ribs, such as 26 and 27, define a recess, as indicated by numeral 30 and 31 at the base or juncture of each rib with their respective wall. Also, the recesses 30 and 31 terminate with a linear surface 32 wherein the adjacent recesses 30 and 31 and linear surface 32 provide a retaining or holding means in cooperation with a retaining element 29 for maintaining impression material in place during and subsequent to the taking of an impression. All of the respective spaces or grooves between adjacent ones of the ribs include the holding means retaining element and this includes all of the ribs integrally formed on walls 11 and 12 respectively. The element may be a wire, plastic strip or the like and extends across the gap or space between adjacent ones of the ribs exteriorly of the ribs.

The retaining or holding means further is illustrated in FIG. 9 wherein it can be seen that each of the respective ribs, such as ribs 26 and 27, include rounded ends, such as illustrated by numeral 33 for the upper end and numeral 34 at the lower end. The sides of the ribs are linear surfaces joining the upper and lower rounded ends. By such a retaining or holding means, the material is held in place and will not move during the impression-taking or during the impression material setup or curing procedure. No irritation or discomfort is experienced by the patient while biting into the impression since there are no sharp exposed corners or edges which the patient could encounter.

Figures 4, 5:
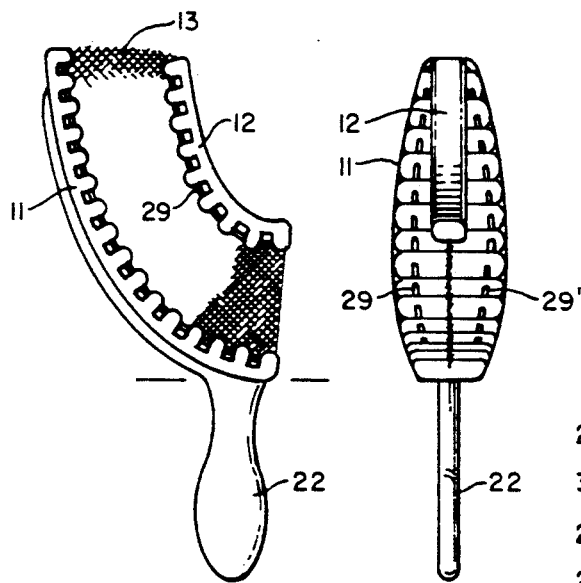
FIG. 4 is a top plan view of another version of another dental tray incorporating the present invention.
FIG. 5 is an end elevational view of the dental tray version shown in FIG. 4.

Referring now in detail to FIG. 4, another embodiment of the invention is shown which represents one-half of the full tray shown in FIG. 1. The construction is identical with the exception that the wire 14 joining the ends of the walls 11 and 12 in FIG. 1 is not used and the tray construction is very flexible so that the impression material will hold the impressed bite without subsequent return to original shape. The membrane 13 supports both the walls 11 and 12. Furthermore, when the impression material has been placed in the work area on both sides of the membrane, additional support is given so that the impression procedure can be achieved. It is to be noted that the ribs and retainer elements, such as ribs 26 and 27, are identical to those shown in FIGS. 8 and 9. It also is to be noted that a wire could be used with the quadrant impression.

Figures 6, 7:
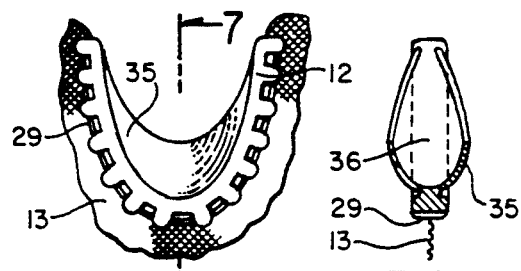
FIG. 6 is a fragmentary plan view of another version of the dental tray incorporating a tongue suppressor.
FIG. 7 is a transverse cross-sectional view of the tongue suppressor shown in FIG. 6 as taken in the direction of arrows 7—7 thereof.

Referring now in detail to FIGS. 6 and 7, a tongue suppressor is illustrated in another version of the invention wherein the suppressor is identified by numeral 35 and is integrated with and as a part of the center wall 12, such as in the embodiment shown in FIG. 1. The suppressor includes forward walls defining a hollow area identified by numeral 36 and the patient's tongue may be inserted into the hollow 36 between the walls to function as a suppressor. Impression material retention ribs and elements are employed as in the other versions.

In view of the foregoing, it can be seen that the novel dental impression tray of the present invention provides a retaining and holding means for the impression material which ensures that the material will not move either during the procedure in which an impression is being taken or subsequent to the procedure. Also, there is no discomfort to the patient because of the holding means and distortion is eliminated through the use of wire and other construction materials having non-memoric characteristics or the elimination of the wire altogether.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A dental impression tray comprising:
   a pair of arcuate walls arranged in parallel spaced-apart relationship defining a working area between opposing wall surfaces;
   an impression material support membrane disposed in said working area and having opposite edge marginal regions attached to said pair of walls so as to divide said working area into an upper section and a lower section;
   impression material retaining means carried on said wall opposing surfaces;
   said retaining means comprising a plurality of ribs substantially perpendicular to said membrane and integral with each of said opposing wall surfaces respectively; and
   said plurality of ribs on each of the wall surfaces arranged in fixed parallel spaced-apart relationship and each rib of said plurality having rounded upper and lower ends connected by a linear surface, said lower section including an undercut recessed notch at said lower end immediately adjacent to said support membrane whereby the gums of the patient are protected from irritation or injury.

2. The invention as defined in claim 1 wherein:
   said arcuate walls include 180 degrees of curvature.

3. The invention as defined in claim 1 wherein:
   said arcuate walls include no more than 90 degrees of curvature.

4. The invention as defined in claim 1 including:
   a hollow tongue suppressor integral with a selected one of said pair of walls immediately behind its associated plurality of ribs.

5. The invention as defined in claim 1 including:
   said opposing wall surfaces having a flat linear surface extending between adjacent ones of said plurality of ribs;
   each of said linear surfaces included in said retaining means.

6. The invention as defined in claim 1 including:
   a metal member of non-memoric characteristics connected between said pair of wall ends.

7. The invention as defined in claim 1 wherein:
   said support membrane is a sheet of plastic embedded with fibrous material.

8. The invention as defined in claim 1 wherein:
   said support membrane is a gauze medium embedded with plastic-like material.

9. The invention is defined in claim 1 including:
   said walls constituting an inner wall and an outer wall;
   a handle carried on said outer wall normal with its plane of attachment with said outer wall.

10. The invention as defined in claim 9 wherein:
    said outer wall is of a predetermined vertical dimension and said inner wall is of a vertical dimension which is substantially less than said outer wall vertical dimension.

11. A dental impression tray providing comfort to a patient and that is non-injurious comprising:
    a pair of arcuate walls arranged in parallel spaced-apart relationship defining a working area between opposing wall surfaces;
    an impression material support membrane disposed across said working area and having opposite edge marginal regions attached to said pair of walls so as to divide said working area into an upper section and a lower section;
    impression material retaining means carried on the opposing wall surfaces of said pair of walls comprising a plurality of spaced-apart elongated ribs integrally formed with each of said walls respectively; and
    each of said ribs being rod-like, substantially perpendicular to said membrane and each rib having a rounded top end and a rounded bottom end and each of said ribs being round in cross-section whereby patient gum encounter with said ribs is free from irritation and injury.

12. The invention as defined in claim 11 wherein:
    said pair of walls include an outer wall having a given height dimension and an inner wall of less height dimension than said outer wall given height dimension whereby said pair of walls are easily accommodated within the mouth of the user.

13. The invention as defined in claim 12 wherein:
    said pair of walls include opposite ends defining open ends respectively in spaced-apart relationship and constituting a rear end disposed towards the rear of a patient's mouth and an opposite end constituting a front end.

14. The invention as defined in claim 13 including:
    an arcuate metal member having its opposite ends attached to said wall ends constituting said rear end in spaced-apart relationship to said support membrane.

15. The invention as defined in claim 14 wherein:
    said support, membrane is a plastic-like material embedded with a medium selected from:
    a. a gauze medium;
    b. a fibrous medium.

16. The invention as defined in claim 15 including:

a handle attached to said outer wall outwardly extending from said outer wall perpendicular to that portion of said outer wall to which said handle is attached.

17. The invention as defined in claim 11 wherein:
said impression material retaining means comprises a retainer element extending between adjacent ones of ribs mid-way between said top end and said bottom end of each rib defining a space between said adjacent ribs and said retainer element and said walls.

18. The invention as defined in claim 17 wherein:
said retainer element is a strip attached on the exterior of said adjacent ribs disposed across the length of said plurality of ribs.

19. The invention as defined in claim 17 wherein:
said retainer element is a wire attached on the exterior of said adjacent ribs disposed across the length of said plurality of ribs.

* * * * *